United States Patent [19]

Chow

[11] Patent Number: 5,024,223
[45] Date of Patent: Jun. 18, 1991

[54] ARTIFICIAL RETINA DEVICE

[76] Inventor: Alan Y. Chow, 191 Palamino Pl., Wheaton, Ill. 60187

[21] Appl. No.: 549,094

[22] Filed: Jul. 6, 1990

Related U.S. Application Data

[63] Continuation-in-part of Ser. No. 390,562, Aug. 8, 1989.

[51] Int. Cl.$^5$ .................... A61N 1/00; A61F 2/14; A61B 17/00
[52] U.S. Cl. .................... 128/419 R; 128/784; 623/4; 606/1; 606/107
[58] Field of Search .................... 128/419 R, 783–785; 623/4, 6; 106/1, 107

[56] References Cited

U.S. PATENT DOCUMENTS

| | | | |
|---|---|---|---|
| 2,760,483 | 10/1954 | Tassicker | 623/4 X |
| 3,594,823 | 7/1971 | Collins | |
| 3,628,193 | 12/1971 | Collins | 128/419 R |
| 3,766,311 | 10/1973 | Boll | 340/407 X |
| 3,848,608 | 11/1974 | Leonard | 128/419 R |
| 3,914,800 | 10/1975 | Collins | 340/407 X |
| 4,251,887 | 2/1981 | Anis | 606/107 X |
| 4,272,910 | 6/1981 | Danz | 623/4 X |
| 4,551,149 | 11/1985 | Sciarra | 623/4 |
| 4,600,004 | 7/1986 | Lopez et al. | 606/1 |
| 4,601,545 | 7/1986 | Kern | 623/4 X |
| 4,628,933 | 12/1986 | Michelson | 128/419 R |
| 4,750,498 | 6/1988 | Graham | 606/107 X |
| 4,836,202 | 6/1989 | Krasner | 606/107 |

OTHER PUBLICATIONS

Science News, Feb. 2, 1974, vol. 105, No. 5, p. 105.
Science, Jul., 1981.

Primary Examiner—Ronald Frinks
Attorney, Agent, or Firm—Willian Brinks Olds Hofer Gilson & Lione

[57] ABSTRACT

A silicon chip device composed of a large array of densely packed microphotodiodes is implanted between the inner and outer retina layers, in patients with vision-deficient eyes suffering from retinal dysfunction, to allow for useful formed vision. The photoactive surface of each photodiode, with its silicon deposited or etched electrode, point towards the incident light. The device produces an amplitude-modulated current to stimulate the inner retinal layer. The device is intrinsically inert due to its doped silicon substrate nature.

20 Claims, 12 Drawing Sheets

ARTIFICIAL RETINA DEVICE

This application is a continuation-in-part application of U.S. Pat. application Ser. No. 390,562 filed Aug. 8, 1989 by Alan Y. Chow, which is incorporated herein by reference.

BACKGROUND OF THE INVENTION

The present invention is directed to a medical product and operation procedure which can be used to correct vision loss or even complete blindness caused by certain retinal diseases. A variety of retinal diseases, for example, cause vision loss or blindness by destruction of the choroid, choriocapillaris, and the outer retinal layers. The outer layers include Bruch's membrane and retinal pigment epithelium, the loss of which results in degeneration of the inner retinal photoreceptor layer. These diseases, however, often spare much of the remaining inner retinal layers of the outer nuclear, outer plexiform, inner nuclear, inner plexiform, ganglion cell and nerve fiber layers.

The current invention involves the use of an electronic device, a photosensitive array, that is capable of mimicking the signals that would otherwise be produced by the damaged inner retinal photoreceptor layer. When the device is implanted between the inner and outer retinal layers, it will stimulate the inner layer to provide significantly useful formed vision to a patient in a manner never before available.

Prior attempts have been made to produce vision by stimulating various portions of the retina. One such attempt involved an externally powered but internally located photosensitive array device with its photoactive surface and electrode surface on opposite sides. The device was to stimulate the nerve fiber layer via direct placement on this layer from the vitreous body side. The success of this device is unlikely due to it having to duplicate the complex frequency modulate neural signals of the nerve fiber layer. Furthermore, the nerve fiber layer runs in a general radial course with many layers of overlapping fibers from different portions of the retina making selection of the appropriate nerve fiber to stimulate extremely difficult if not impossible. The production of useful formed visual imagery is therefore highly unlikely. No device of this type has been known to have been constructed that produced any type of formed image.

Another prior device involved a unit consisting of a supporting base onto which a photo-sensitive material such as selenium is coated. This device was to have been inserted through an external scleral incision made at the posterior pole resting between the sclera and choroid or between the choroid and retina. Light stimulation would then cause a potential to develop on the photosensitive surface causing ions to be produced which would then theoretically migrate into the retina causing stimulation. However, having no discrete surface structure to restrict the directional flow of charges, lateral migration and diffusion of charges would be allowed thereby preventing any resolution capability. Placement of this device between the sclera and choroid would also virtually block the discrete migration of ions to the photoreceptor and inner retinal layers due to the presence of the choroid, choriocapillaris, Bruch's membrane and the retinal pigment epithelial layer. Placement of the device between the choroid and the retina would still interpose Bruch's membrane and the retinal pigment epithelial layer in the pathway of discrete ion migration. Also, as this device would have had to be inserted into or through the highly vascular choroid of the posterior pole, severe subchoroidal, intraretinal and or intraorbital hemorrhage would likely have resulted along with disruption of blood flow to the posterior pole. One such device was apparently constructed and implanted into a patient's eye resulting in reported light perception but no formed imagery.

SUMMARY OF THE INVENTION

The artificial retina device of this invention circumvents the limitations of previous devices. It is composed of a plurality of discrete photodiodes with their individual electrodes disposed on one surface of a substrate, the photodiodes each being connected to a common electrical ground on the other side of the substrate. Each photodiode includes an active electrode layer overlaying a photosensitive layer, and each is connected to an electrical ground. The photodiodes have electrical outputs that correspond to the amplitude of the light incident on said device, whereby said device can be implanted in the eye intermediate the inner retinal layer and the retinal pigment epithelium of outer layer of the retina, so that each of said photodiodes will stimulate directly individual or small groups of cells in the inner retinal layer corresponding to the light incident on said device.

When inserted within the retina between the inner and outer retinal layers, in the potential space zone, an amplitude-modulated electric potential, varying with illumination, produced by each photodiode will stimulate the overlying inner retinal layer consisting of photoreceptors, bipolar cells and horizontal cells. As these cells normally both receive and produce analog amplitude-modulated currents, the analog amplitude-modulated output of the device is well suited for stimulation of these cells. The amplitude-modulated signals of the bipolar cells are then modified and converted by the amacrine and ganglion cells to a frequency-modulated signal as is the normal biological event in the innermost area of the inner retinal layer for distant transmission through the optic nerve to the lateral geniculate area of the brain. Because the complex conversion of the amplitude-modulated signal to the frequency-modulated signal is left to intrinsic retinal mechanisms, the formed vision produced is much enhanced compared to devices that attempt to stimulate the nerve fiber layer directly with electronic and amplifier reconstructed frequency-modulated signals.

Such a device has been fabricated and successfully implanted in the intraretinal space of several rabbit eyes. Electrical responses produced by the overlying retina following stimulation of the implant, compatible with visual function, has also been recorded.

BRIEF DESCRIPTION OF THE DRAWINGS

FIG. 1C–[4] are perspective views of four alternative embodiments of the present invention;

DETAILED DESCRIPTION OF THE PRESENTLY PREFERRED EMBODIMENTS

Figure 1A:
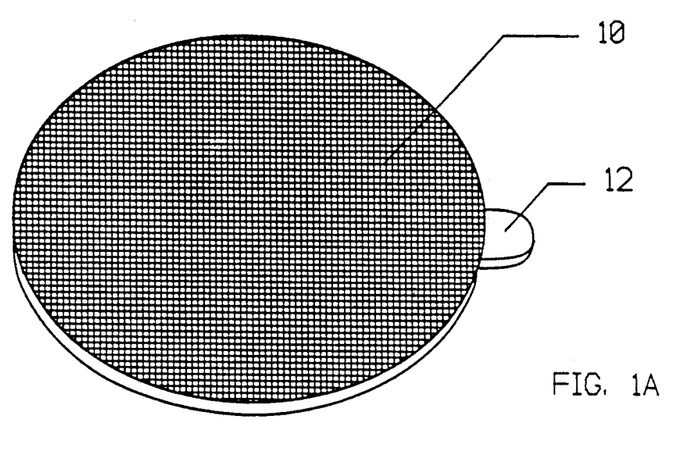
FIG. 1A is a perspective view of an artificial retina device of the present invention.
Figure 1B:
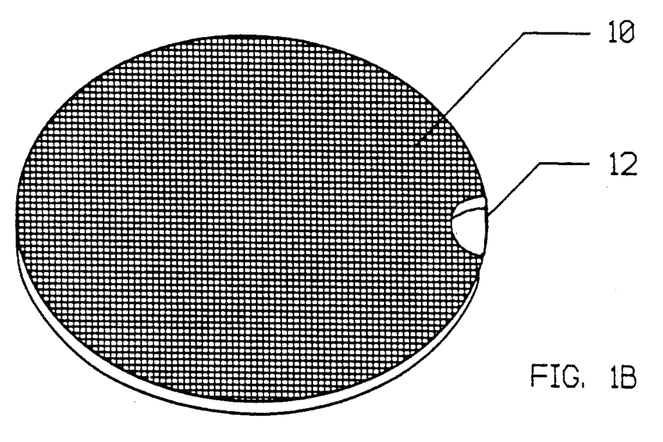
FIG. 1B is a perspective view of an alternative form of an artificial retina device of the present invention.
Figure 1C:
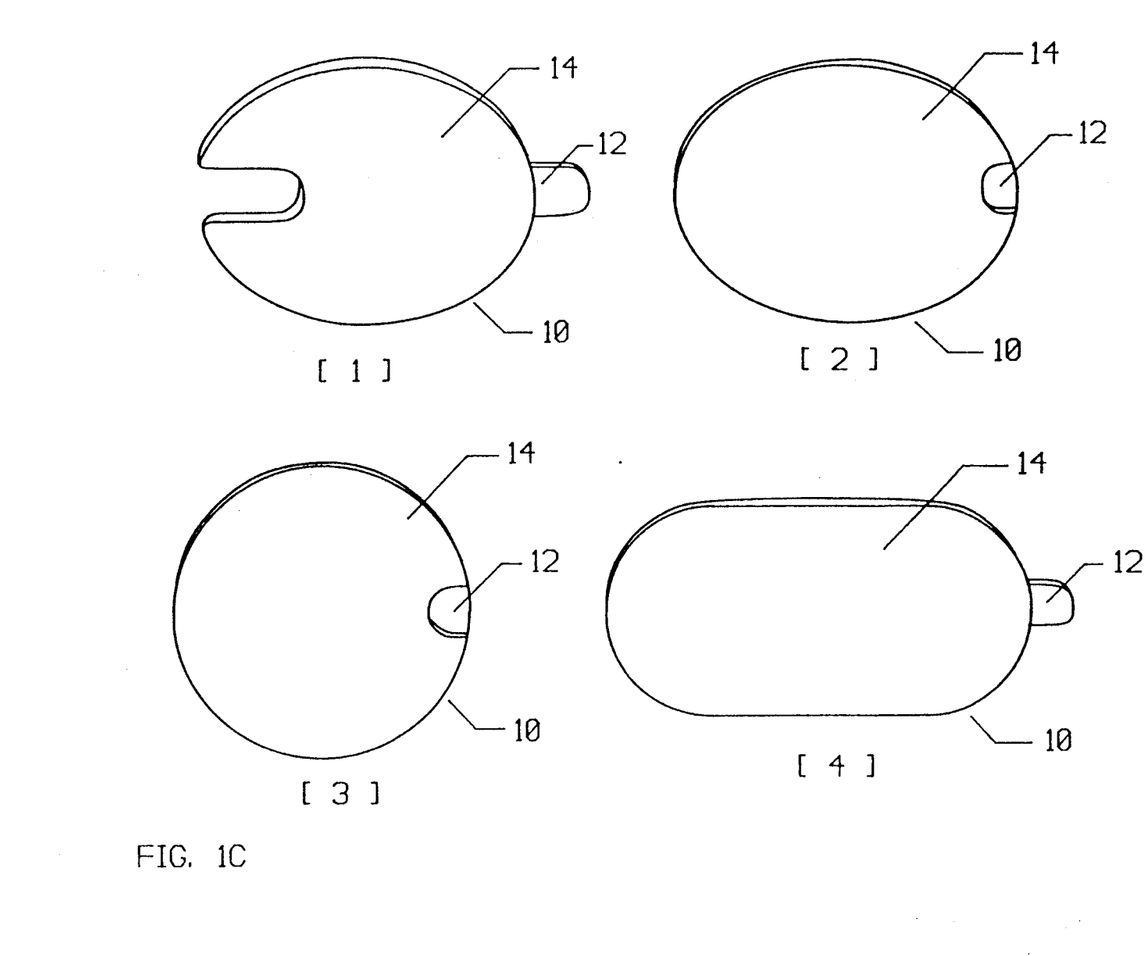

In one embodiment of this invention, an artificial retina device 10 is generally circular in shape with an integral grasping member (FIG. 1B) or a projecting grasping member (FIG. 1A) to grasp the device while it is being inserted. The device ranges from 2 mm to 20 mm in diameter and from 0.005 mm to 2 mm in thickness.

As shown in FIG. 1C, the device 10 may be round (FIG. 1C), oval (FIG. 1C) elliptical (FIG. 1C), or irregular (FIG. 1C) in shape. The surface contours may be flat or curved to match the curvature of the retina. The edges or selected areas of the anterior 14 or posterior 16 (FIG. 2A) surfaces may be fashioned with ridges or other protrusions to improve stability within the retina and to improve biological acceptability. The device may also have ledges, lips or loops to aid manipulation during implantation. In addition, it may also have openings (not shown) between the two surfaces to allow passage of intraretinal nourishment and tissue ingrowth to maintain the device securely in the retina.

Figure 1D:
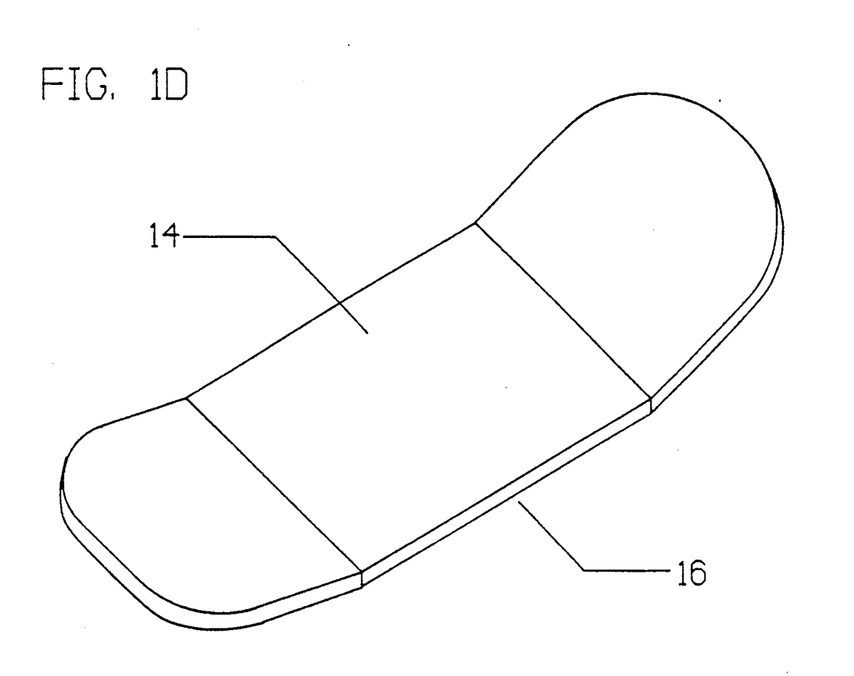
FIG. 1D is a perspective view of an artificial retinal device comprised of several smaller devices secured together in a linear and articulated fashion.

The device may also be comprised of multiple smaller devices joined together by their edges. In one embodiment (FIG. 1D) three devices may be joined together in an articulated fashion to increase implant size and to conform to the curved retina. The devices are joined with an inert adhesive such as a silicon cement. The concavity of the articulated device is the anterior surface facing incoming light (14) and the convexity of the device is the posterior surface facing the retinal pigment epithelium (16).

Figure 1E:
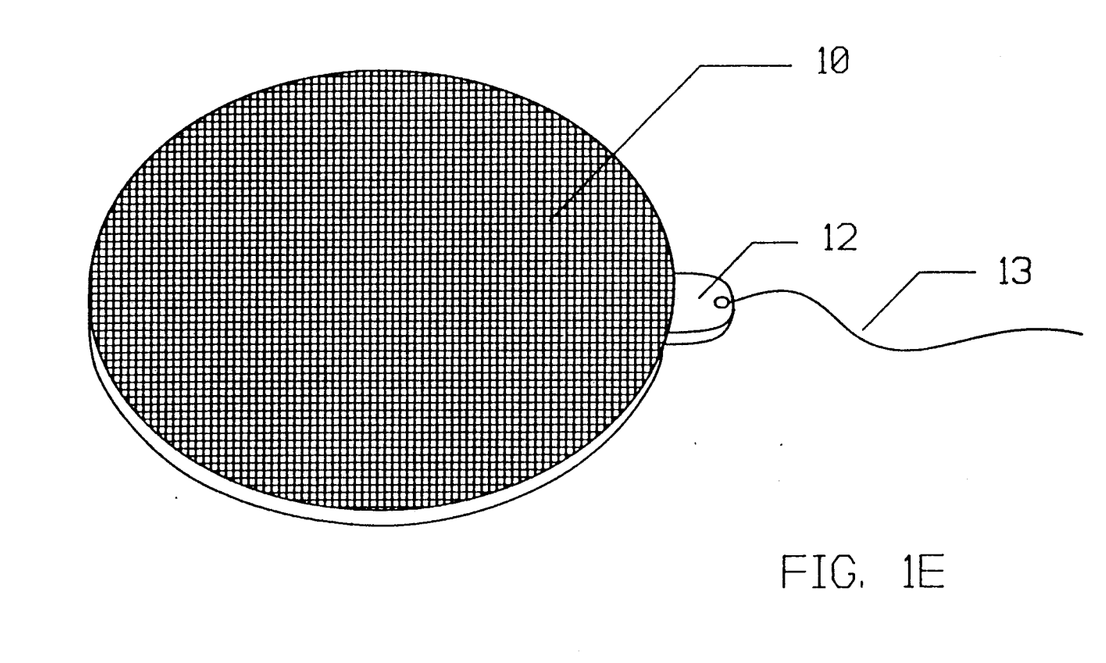
FIG. 1E is a perspective view of an artificial retinal device with a thin suture attached for retrieval purposes.

A device 10 may also have a flexible member such as a thin suture 13 attached (FIG. 1E) to facilitate removal of the implant as needed. Suture 13 is fashioned from an inert material such as nylon and may be left in place or removed via traction on the suture while securing the implant.

Figures 5, 6:
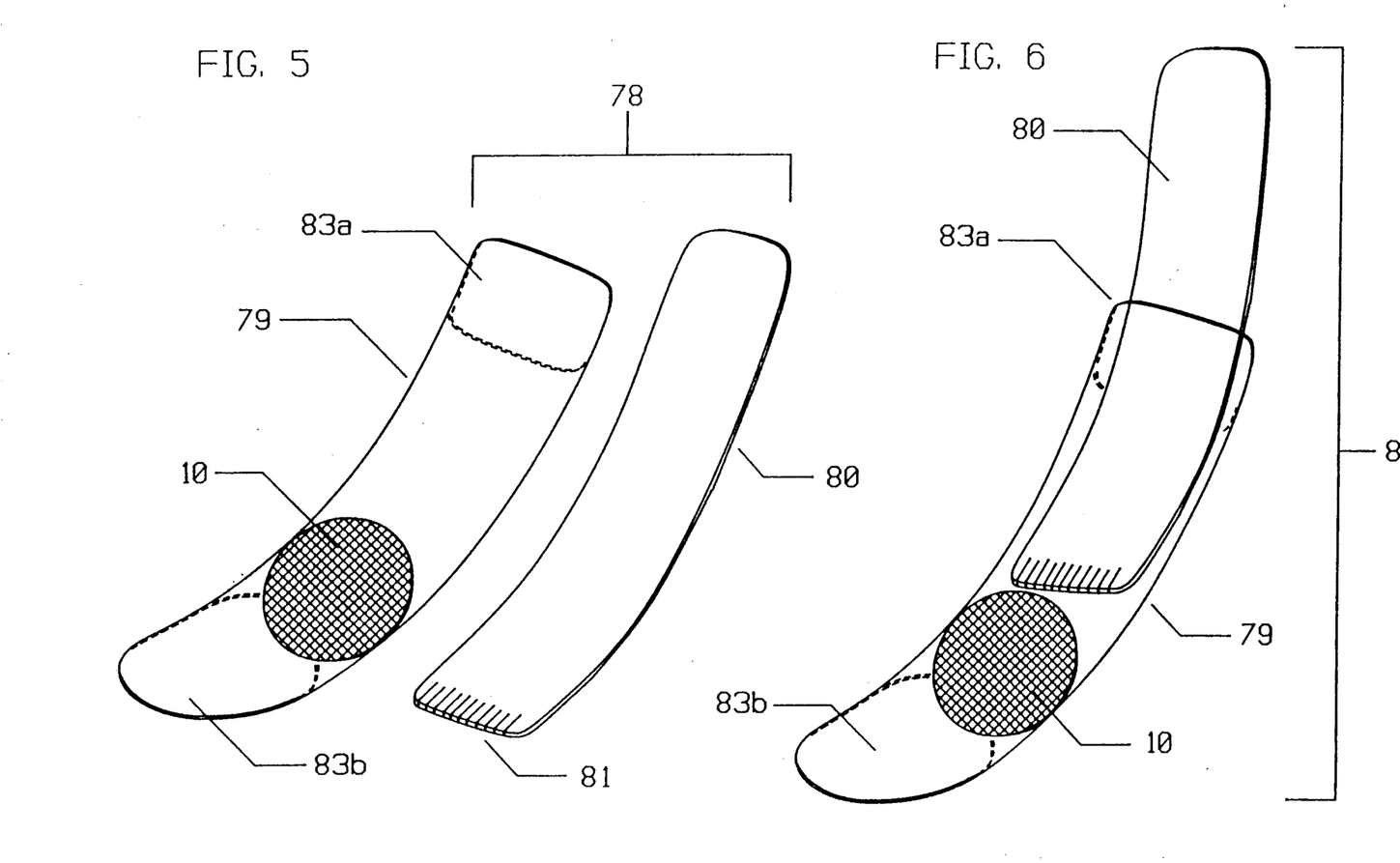
FIG. 5 is a perspective view of the separate components of an insertion guide that may be used to insert the implant into the eye.
FIG. 6 is a perspective view of the assembled components of the insertion guide of FIG. 5.

As shown in FIG. 5, an insertion guide 78 may be used to insert implant 10 into the eye. The guide portion 79 of the device is an elongated, flattened tubular structure fashioned from a curved and compressed tube of clear flexible material such as TEFLON (polytetrafluoroethylene) or polyethylene with lips 83a and 83b at each end. The pusher portion 80 of the device is adapted to slide through guide portion 79, and is made from a similar material. Pusher 80 has multiple serrations 81 at one end to allow positive contact while pushing implant 10. In operation, implant 10 is placed within the guide 79 followed by pusher 80. The completed assembly 82 (FIG. 6) is inserted into the desired intraretinal location via a scleral incision into the intraretinal space. The pusher 80 is then pushed while retracting the guider 79 thus depositing the implant pass lip 83b into the intraretinal space. With device 78, lip 83b can be used to lift and separate the desired retinal layers, and be used to deposit the implant accurately in the desired location.

Figure 2A:
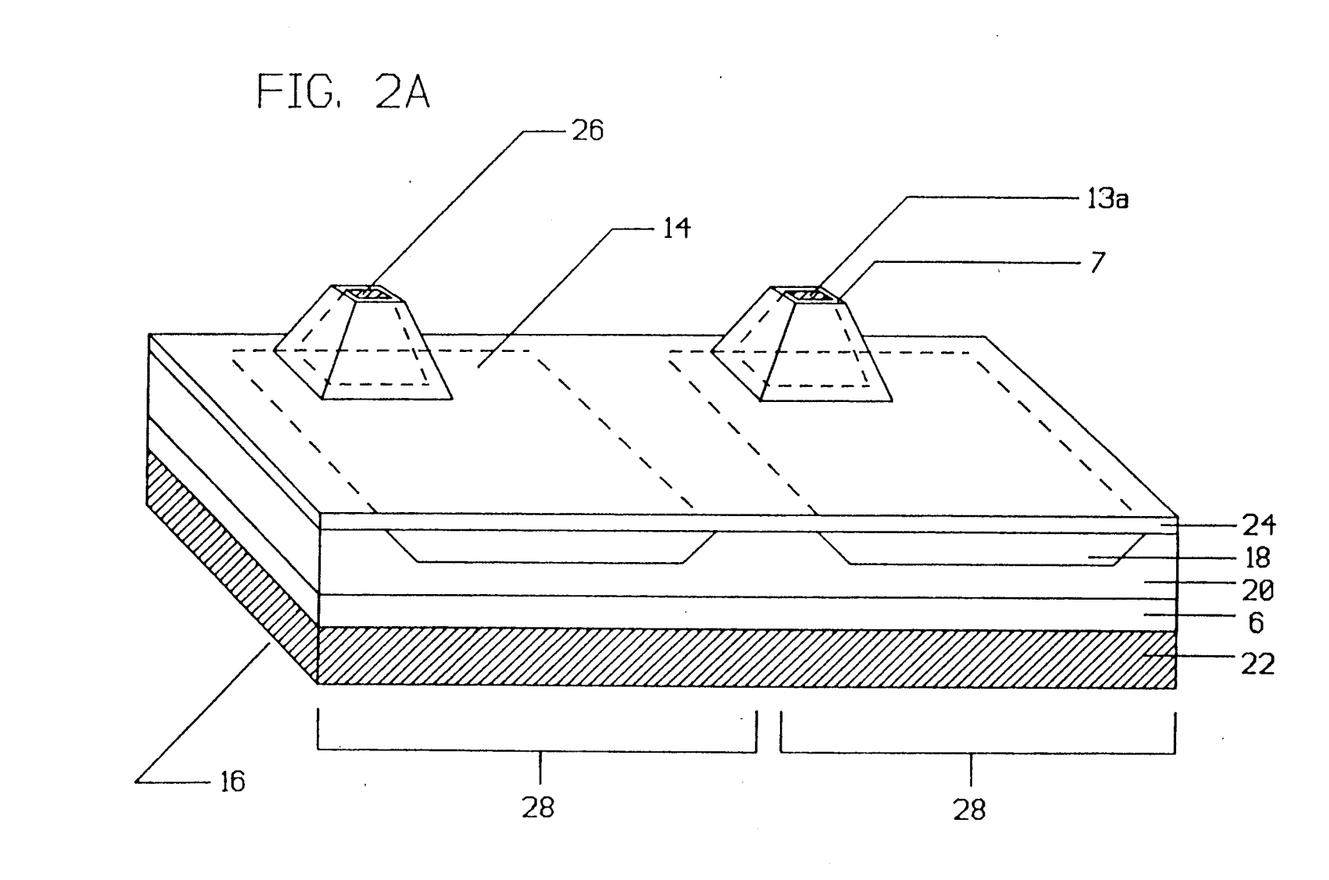
FIG. 2A is a perspective, cross-sectional view of a first photodiode array for use in an artificial retina device of the present invention.
Figure 2B:
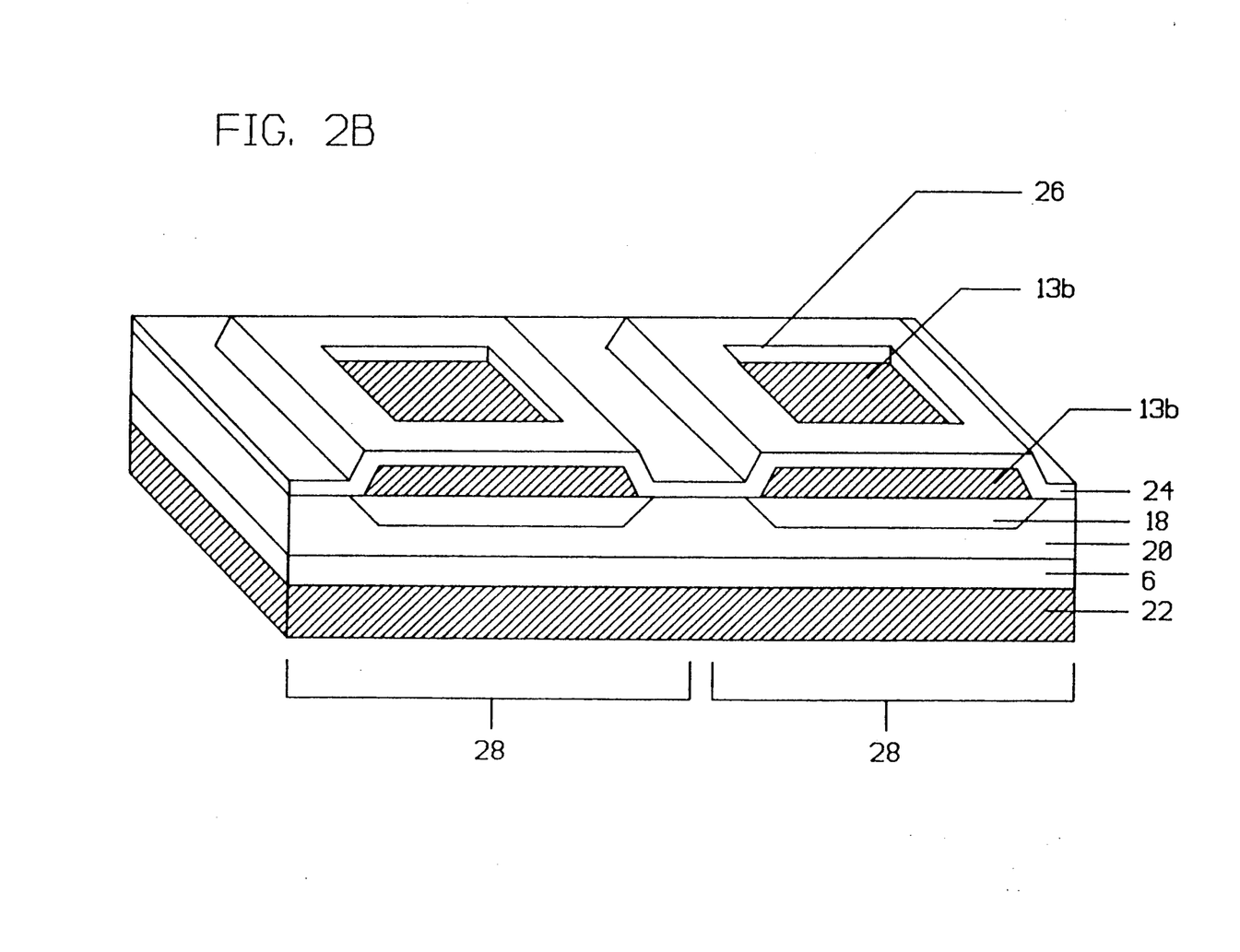
FIG. 2B is a perspective, cross-sectional view of a second photodiode array for use in an artificial retina device of the present invention.

As shown in FIGS. 2A and 2B, the details of the photodiode construction of the artificial retina device of the present invention consist of multiple layers of both pure and doped silicon deposited and etched. An insulated or noninsulated polysilicon active electrode structure 13a projects from the surface in one embodiment (FIG. 2A), or a flat polysilicon active electrode surface 13b is constructed in another alternative embodiment (FIG. 2B) to transfer a current from the photodiode to the overlying photoreceptor, bipolar and inner retinal cell layers as explained in detail below. In particular, the polysilicon electrode structure 13a or 13b can be made by standard semiconductor plasma and/or wet etch techniques.

In another embodiment of the invention (FIG. 2C), a chromium base 72 and a gold surface 71 may be substituted for the conductive surfaces of the active electrode and common electrical ground. This embodiment, a NiP device, employs a P-type substrate 75. A layer of chromium 72 is deposited on the posterior electrical ground surface followed by deposition of a layer of gold 71. A P+ layer 78 is then ion-implanted onto the anterior surface followed by ion implantation of individual N tubs 77. An automatic i layer forms at the junction of the N and P+ and N and P layers. A thin layer, transparent to light, of chromium 72 and then gold 71 is deposited over each N tub 77. This produces a NiP device. The N and P layers may be reversed to produce a PiN device. A PiN device would not require ion implantation of a P+ layer 78.

Figure 2C:
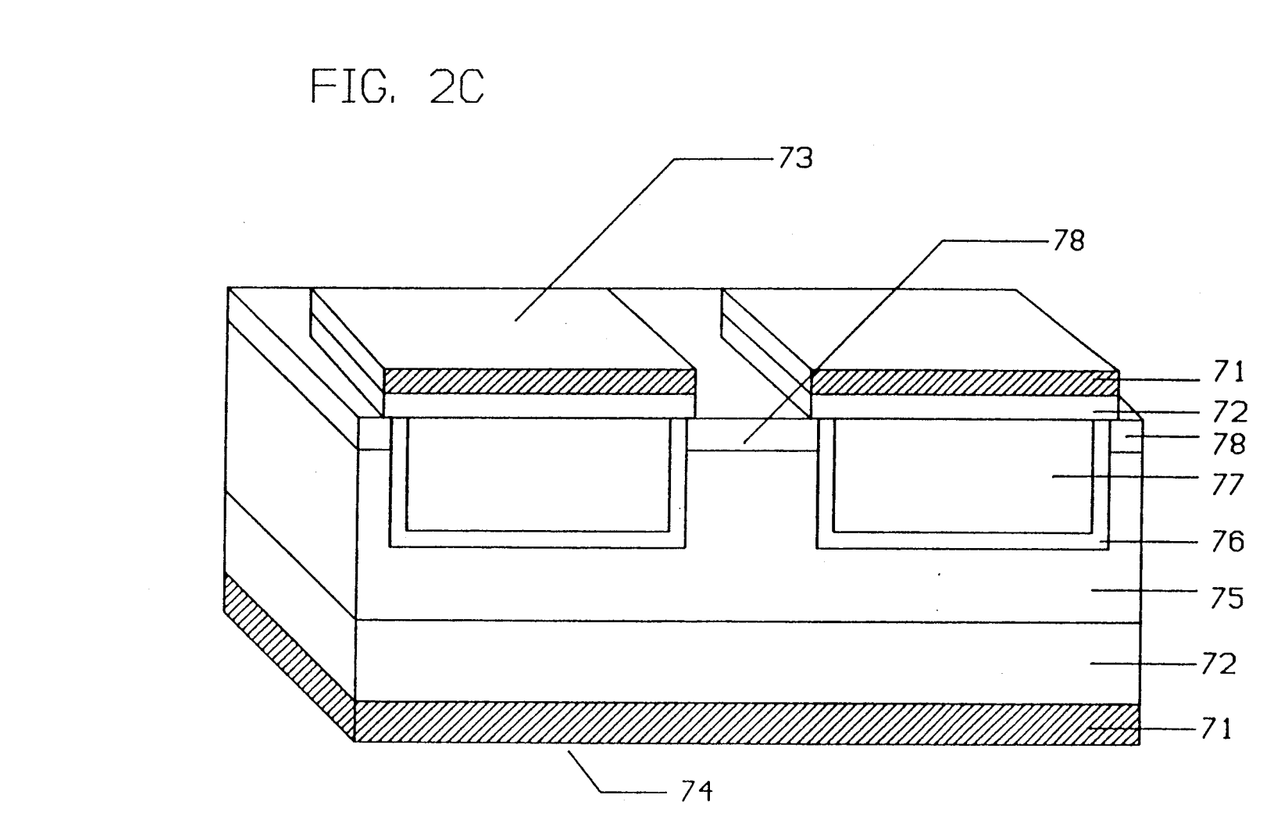
FIG. 2C is a perspective, cross sectional view of a third type of photodiode array arrangement used in the artificial retina device of the present invention.

Other conductive materials can be used as well for these layers: aluminum, platinum, conductive silicon or combinations of these materials.

The artificial retina device of the present invention is, therefore, a large array of photovoltaic microphotodiodes of the PiN type. Each microphotodiode (FIGS. 2A and 2B) consists of a shallow P-doped photoactive layer 18 overlaying an intrinsic layer 20 which in turn overlays a N-doped layer 6. On the posterior surface of layer 6 is deposited a conductive layer 22 of polysilicon that forms the common complimentary electrode or ground. A common complimentary electrode is shown, but the device can be constructed with a discrete complimentary electrode for each microphotodiode.

On the anterior surface is deposited a layer of silicon nitrate 24 covering the entire surface except for openings (or on the unmasked areas) 26 that establish electrode contact areas for the polysilicon active electrode 13a (or 13b). The PiN layers may be reversed (NIP) or modified to facilitate reversal of the device polarity. As can be seen in FIGS. 2A and 2B, a plurality of nodes 28 are formed from a plurality of microphotodiodes described above. The designed current output of each self-powered photodiode node is on the order of 50 nA when the device is exposed to average room lighting. However, the electrical current output may be designed to be greater or less than this value depending upon the stimulation requirement of the overlying cell layer. A supplemental bias activation current may also be provided by an insulated wire or series of insulated wires leading from the device from the eye into an external or internally implanted battery unit.

Figure 3A:
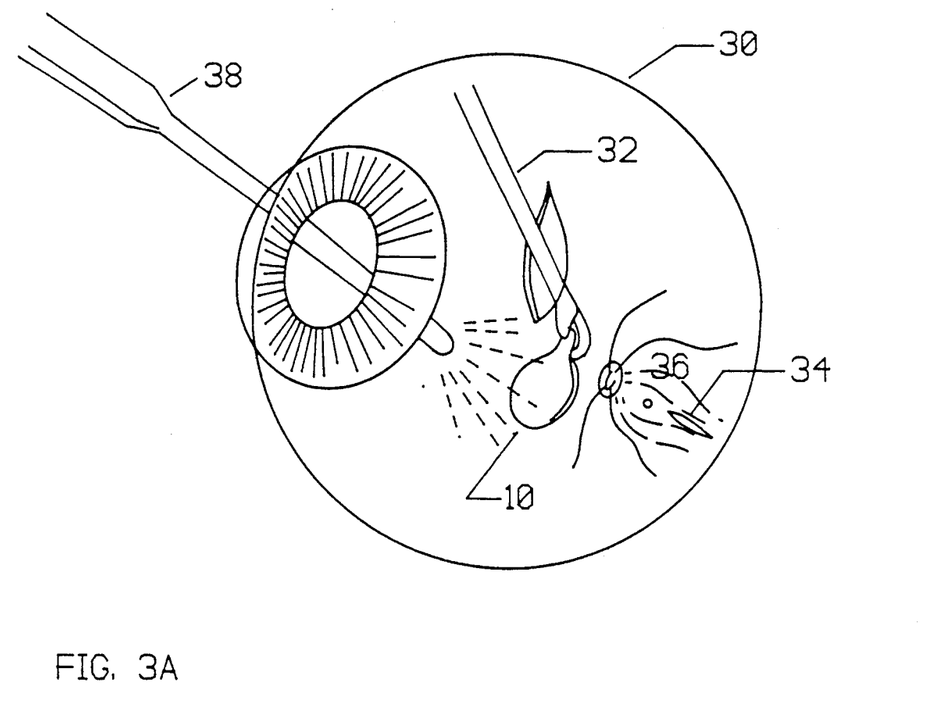
FIG. 3A-3C illustrate steps in a surgical procedure for implanting an artificial retina device of the present invention.
Figure 3B:
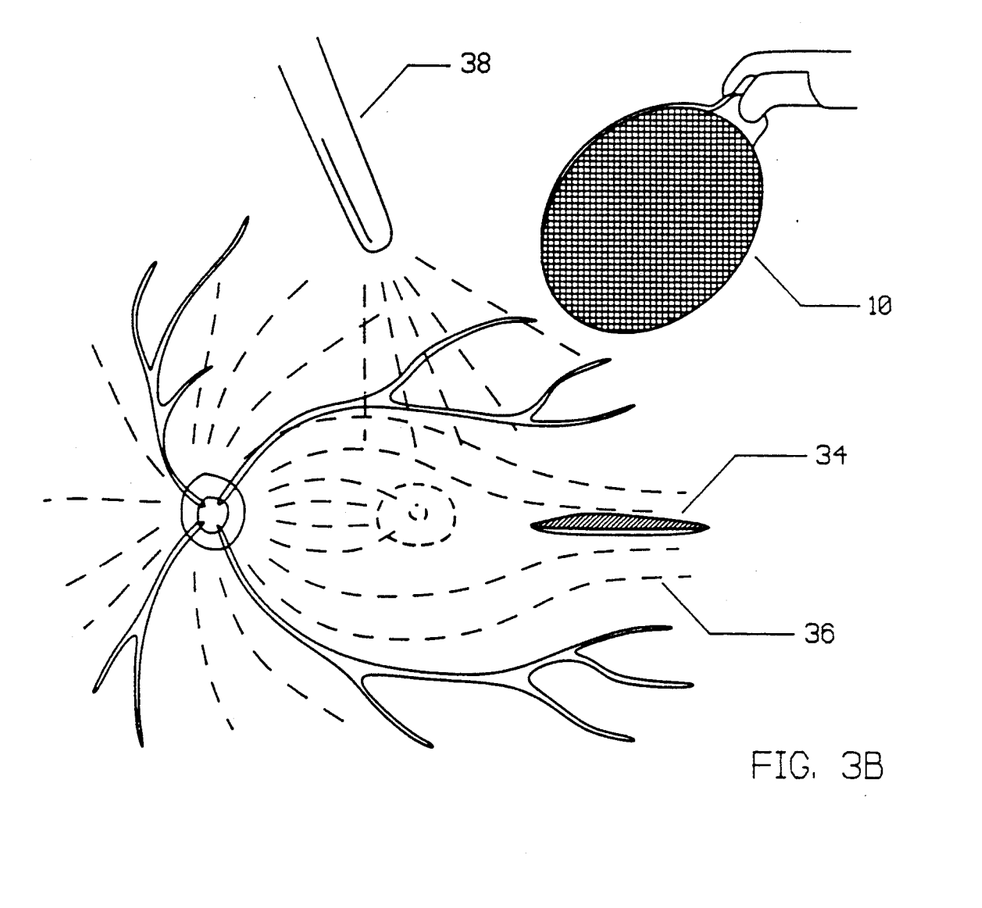

As shown in FIG. 3A, the device 10 of this invention is inserted into the vitreous cavity of the eye 30 via a pars plana incision 32. A horizontal incision 34 (FIG. 3B) is then made through the retina from the vitreous side in the temporal portion of the posterior pole into the potential space between the photoreceptor layer and the retinal pigment epithelium. A horizontal incision 34 made at this location will avoid cutting inner retinal vasculature and will be parallel to coursing nerve fiber layers 36, therefore, also avoiding their injury. Illumination for the surgical procedure is provided by a optical fiber light pipe 38. The potential space is then be opened by canula irrigation of a balanced salt solution into the intraretinal space.

The device is then placed into the intraretinal cavity (FIG. 3C) at the posterior pole under the macula area. Specifically, the device is placed between the retinal pigment epithelium 58 (FIG. 4) and photoreceptor layer 54, or if photoreceptor layer 54 is atrophied or lost then between the retinal pigment epithelium 58 and the bipolar and horizontal cell layer 52. The device is positioned such that the electrical ground 22 (or 74) is overlaying the retinal pigment epithelium 58 and the active electrode 13a (or 13b or 73) faces the incident light.

Figure 3C:
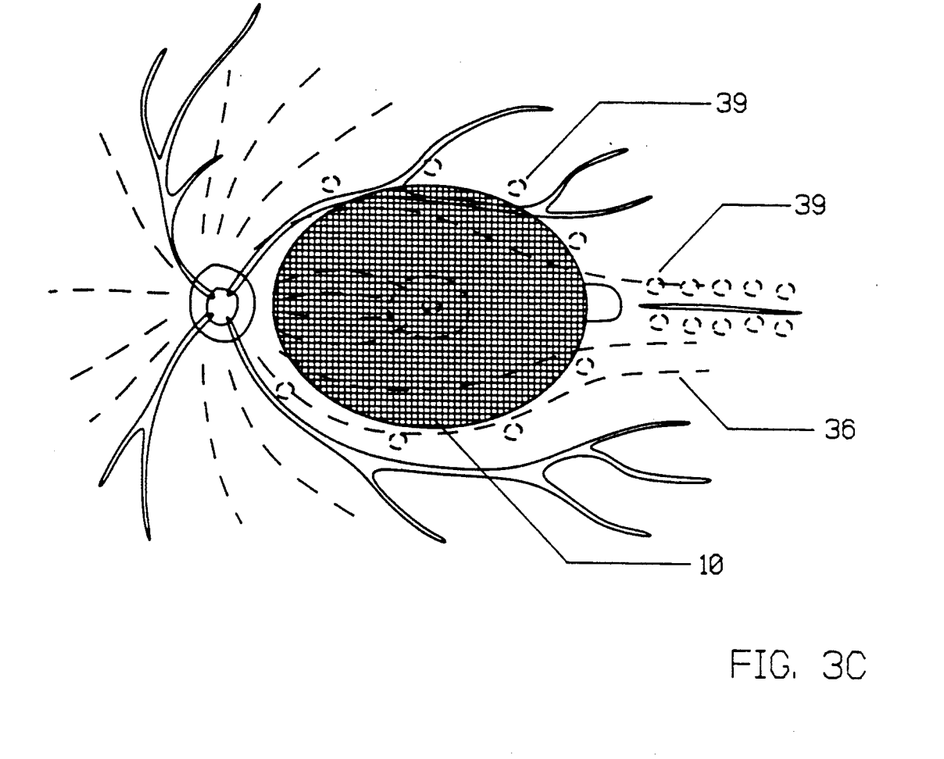

After insertion, a series of endolaserphtocoagulation or endocautery burns 39 are made around the periphery of the device to secure the device. The scar tissue so formed around the periphery of the device will prevent the device from moving out of position. Endolaserphotocoagulation or endocautery 39 may also be used to seal the retinal incision. Air or other approved gaseous compounds may also be injected into the vitreous cavity to tamponade the retinal opening during healing. The pars plana incision will be closed in the usual surgical manner.

An alternate method for implantation would involve making an incision through the sclera just posterior to the ora serata. Dissection would proceed through the choroid, choriocapillaris, Bruch's membrane and retinal pigment epithelium under stereo operating microscope control into the potential space between the inner and outer retinal layers. The artificial retinal implant would then be inserted into this space and directed posteriorly towards the macula by a pushing action imparted by a formed curved iris spatula or by use of the insertion guide 78. The device will rest in the macula area of posterior pole of the eye between the inner and outer retinal layers.

Figure 4:
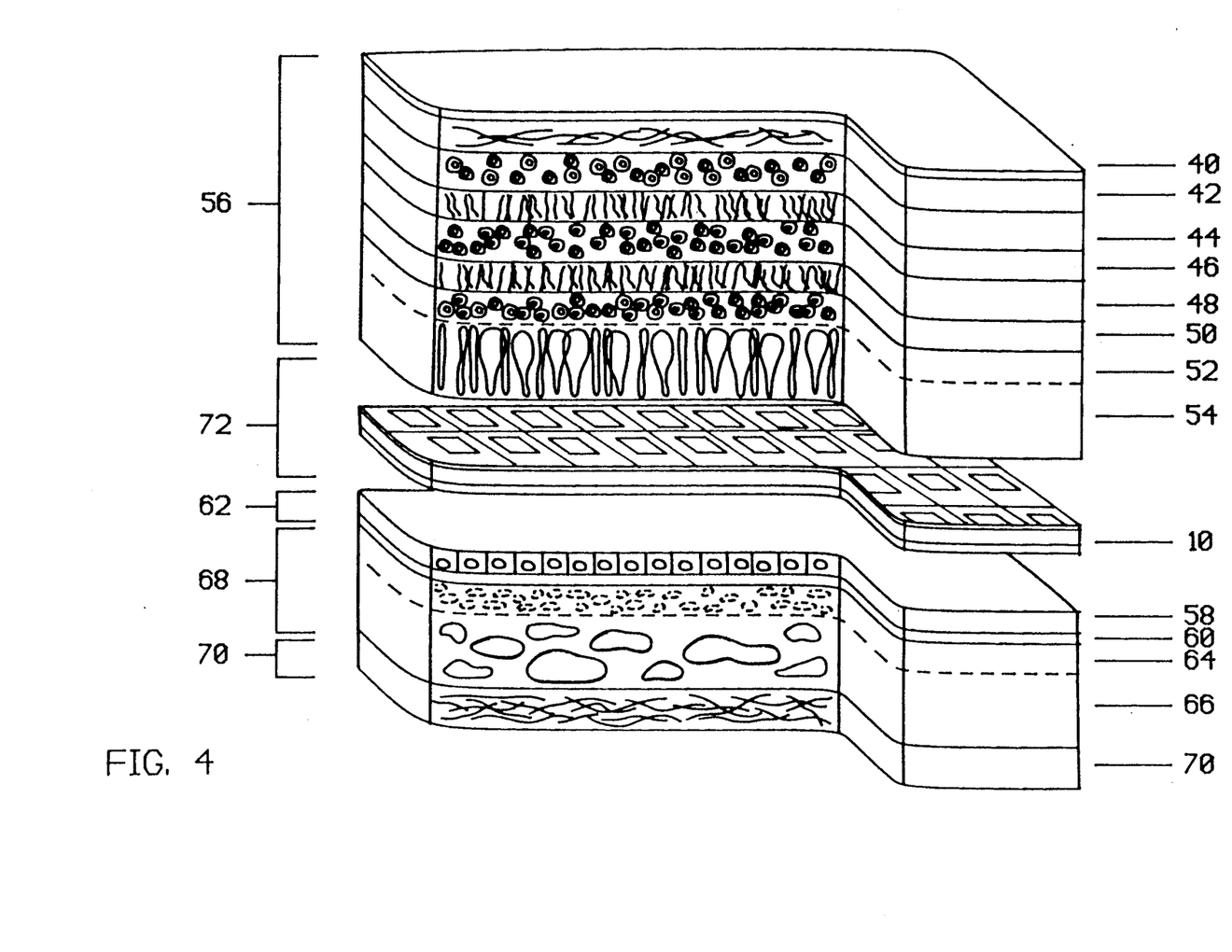
FIG. 4 is an exploded, cross-sectional view of an artificial retinal device of the present invention as implanted in the eye.

The layers of the eye at the posterior pole from inside to outside are shown in FIG. 4: internal limiting membrane 40, nerve fiber layer 42, ganglion and amacrine cell layer 44, inner plexiform 46, inner nuclear layer 48, outer plexiform 50, outer nuclear and bipolar cell layer 52, and photoreceptor layer 54, all of which constitute the inner retinal layer 56. The retinal pigment epithelium 58, and Bruch's membrane 60 constitute the outer retinal layer 62. The choriocapillaris 64, and choroid 66 comprise the choroidal vasculature 68. The outer coat of the eye is the sclera 70.

With regard to FIG. 4, when the device 10 is inserted within the retina between the inner retinal layer 56 (that may or may not contain a functional photoreceptor layer 54) and the outer retinal layer 62, in the potential space zone 72, an amplitude-modulated current varying with illumination, produced by each photodiode of the device 10 will stimulate the overlying inner retinal layer consisting of photoreceptors (if present) and their cell bodies 54, 52, bipolar cells 48 and horizontal cells 52. As cells 48–52 normally both receive and produce analog amplitude-modulated currents, the analog amplitude-modulated output of the device is well suited for stimulation of these cells. The amplitude-modulated signals of the bipolar cells 48 are then modified and converted by the amacrine and ganglion cells 44 to a frequency-modulated signal as is the normal biological event in the innermost area of the inner retinal layer for distant transmission through the optic nerve to the lateral geniculate area of the brain.

As the output of each photodiode will be automatically amplitude modulated corresponding to the intensity of the incident light, the resulting stimulation and signal current production of the overlying photoreceptor or bipolar cell layer will also be amplitude modulated thereby duplicating the normal amplitude-modulated character of these cells. Stimulating inner retina 56 at the above indicated location will also allow the normal function of the horizontal cell on-off receptor fields thereby allowing contrast appreciation.

Although recognizable color information output may not occur from the stimulated cells, significant formed vision output should develop serving as input for the amacrine and ganglion cell layers which will modify the signal into a frequency modulated signal for transmission to the lateral geniculate area of the brain.

While several embodiments of this invention are described, others will be apparent to those of ordinary skill in the art. Such other embodiments are to be included within the scope of the present invention, unless the claims that follow expressly state otherwise.

I claim:

1. An artificial retina device, comprising: a plurality of discrete photodiodes, disposed on one surface of a substrate said photodiodes each including an active electrode layer overlaying a photosensitive layer, each photodiode being connected to an electrical ground, wherein said active electrode layer and ground are made from materials selected from aluminum, platinum, chromium, gold, conductive silicon, or combinations thereof, said photodiodes having electrical outputs that correspond to the amplitude of light incident on said device, whereby said device can stimulate individual or small groups of cells in the inner retinal layer of the eye, corresponding to the light incident on said device.

2. An artificial retina device, comprising: a plurality of discrete photodiodes disposed on one surface of a substrate, said photodiodes each including an active electrode layer overlaying a photosensitive layer, each photodiode being connected to an electrical ground, said photodiodes having electrical outputs that correspond to the amplitude of the light incident on said device, whereby said device can be implanted in the eye intermediate the inner retinal layer and the retinal pigment epithelium of outer layer of the retina, so that each of said photodiodes will stimulate directly individual or small groups of cells in the inner retinal layer corresponding to the light incident on said device, wherein the edges of said implant are rounded to facilitate insertion into the intraretinal space without tearing the retina.

3. The artificial retina device of claim 1, wherein said device is from 2 mm to 20 mm in its maximum width, and from 0.005 mm to 2 mm between said two surfaces.

4. The artificial retina device of claim 1 that further includes a grasping member.

5. The artificial retina device of claim 1 further including a plurality of openings between said two surfaces.

6. The artificial retina device of claim 1 wherein one or both surfaces are curved.

7. The retinal implant device of claim 1, wherein said first surface includes a plurality of protuberances that extend therefrom.

8. An artificial retina device, comprising: a plurality of discrete photodiodes disposed on one surface of a substrate, said photodiodes each including an active electrode layer overlaying a photosensitive layer, each photodiode being connected to an electrical ground, said photodiodes having electrical outputs that correspond to the amplitude of the light incident on said device, whereby said device can be implanted in the eye intermediate the inner retinal layer and the retinal pigment epithelium of outer layer of the retina, so that each of said photodiodes will stimulate directly individual or small groups of cells in the inner retinal layer corresponding to the light incident on said device, wherein said device includes a flexible member extending therefrom.

9. The retinal implant device of claim 8, wherein said flexible member comprises a suture.

10. An artificial retina device, comprising: a plurality of discrete photodiodes disposed on one surface of a substrate, said photodiodes each including an active electrode layer overlaying a photosensitive layer, each photodiode being connected to an electrical ground, said photodiodes having electrical outputs that correspond to the amplitude of the light incident on said device, said device including plural articulated portions so as to conform to a curved retinal layer, whereby said device can be implanted in the eye intermediate the inner retinal layer and the retinal pigment epithelium of outer layer of the retina, so that each of said photodiodes will stimulate directly individual or small groups of cells in the inner retinal layer corresponding to the light incident on said device.

11. The retinal implant device of claim 10 wherein said articulated portions include at least one flexible joint.

12. An artificial retina device, comprising: a plurality of discrete PiN or NiP photodiodes disposed on one surface of a substrate, said photodiodes each including an active electrode layer overlaying a photosensitive layer, each photodiode being connected to an electrical ground, said photodiodes having electrical outputs that correspond to the amplitude of the light incident on said device, the resistances of said photodiodes ranging from 1 ohm-cm to 50,000 ohm-cm, whereby said device can be implanted in the eye intermediate the inner retinal layer and the retinal pigment epithelium of outer layer of the retina, so that each of said photodiodes will stimulate directly individual or small groups of cells in the inner retinal layer corresponding to the light incident on said device.

13. A surgical procedure for implanting into the eye an artificial retina device including a plurality of discrete photodiodes, said procedure comprising:
making a horizontal incision temporal to the macula, parallel to and through the nerve fiber layer;
opening the potential space within the retina;
inserting said device into said space intermediate the inner retinal layer and the retinal pigment epithelium of the outer layer of the retina with said photodiodes facing light incident into the eye; and
closing said incision and space.

14. The surgical procedure of claim 13 wherein said device is inserted into said space by inserting a tubular insertion guide through said incision and into said space, and passing said device through said insertion guide into said space.

15. The surgical procedure of claim 14 wherein said tubular insertion guide is a flattened tube, and said device is passed through said tube by pushing it with a pusher member.

16. The surgical procedure of claim 14 wherein said guide includes a lip on one end that is introduced into said space before said device is passed through it, said lip adapted to deposit said device in the desired location.

17. The surgical procedure of claim 15 wherein said guide and pusher member are curved.

18. The surgical procedure of claim 13 wherein said device is positioned on the macula area of the posterior pole of the eye.

19. A device for implanting an artificial retina device into the eye, comprising:
an elongated flattened tubular member curved along its length with a lip on one end;
a pusher member adapted to slide within said elongated tubular member whereby an artificial retina device can be implanted into the eye through an incision by introducing said tubular member through said incision, and pushing the retina device through said tubular member with said pusher member until said retina device is adjacent said lip.

20. The device of claim 20 wherein said pusher member has serrations at one end.

* * * * *